United States Patent
Murphy et al.

(10) Patent No.: US 11,227,385 B2
(45) Date of Patent: Jan. 18, 2022

(54) METHODS OF CLASSIFYING AND/OR DETERMINING ORIENTATIONS OF OBJECTS USING TWO-DIMENSIONAL IMAGES

(71) Applicant: Loyola University Chicago, Maywood, IL (US)

(72) Inventors: Michael Patrick Murphy, Downers Grove, IL (US); Cameron James Killen, Chicago, IL (US); Karen Wu, Chicago, IL (US)

(73) Assignee: Loyola University Chicago, Maywood, IL (US)

( * ) Notice: Subject to any disclaimer, the term of this patent is extended or adjusted under 35 U.S.C. 154(b) by 0 days.

(21) Appl. No.: 16/535,566

(22) Filed: Aug. 8, 2019

(65) Prior Publication Data
US 2020/0082526 A1 Mar. 12, 2020

Related U.S. Application Data

(60) Provisional application No. 62/715,891, filed on Aug. 8, 2018, provisional application No. 62/818,929, filed on Mar. 15, 2019.

(51) Int. Cl.
*G06T 7/00* (2017.01)
*G06T 7/62* (2017.01)
*G06T 7/73* (2017.01)

(52) U.S. Cl.
CPC .............. *G06T 7/0012* (2013.01); *G06T 7/62* (2017.01); *G06T 7/74* (2017.01);
(Continued)

(58) Field of Classification Search
CPC ......... A61B 6/032; A61B 6/487; A61B 6/505; A61B 6/5217; G16H 50/30;
(Continued)

(56) References Cited

U.S. PATENT DOCUMENTS

| | | | |
|---|---|---|---|
| 2005/0010106 A1* | 1/2005 | Lang ...................... | A61B 6/469 600/425 |
| 2008/0056552 A1* | 3/2008 | Muller ................ | A61B 5/4528 382/132 |

(Continued)

FOREIGN PATENT DOCUMENTS

| | | |
|---|---|---|
| EP | 2801320 | 6/2018 |
| JP | 2009195490 | 9/2009 |

(Continued)

OTHER PUBLICATIONS

International Search Report & Written Opinion for International Application No. PCT/US2019/045668, dated Nov. 28, 2019, 12 pages.

*Primary Examiner* — Ian L Lemieux
(74) *Attorney, Agent, or Firm* — Hartman Global IP Law; Gary M. Hartman; Domenica N. S. Hartman

(57) ABSTRACT

Methods for classifying and measuring orientations of objects, as nonlimiting examples, implants utilizing two-dimensional radiographs. One such method determines a three-dimensional orientation of an object based on its area projected onto a two-dimensional image and known or measured geometry. Another such method provides an automated solution to computationally determine the orientation and characterizing features of an implant based on two-dimensional radiographs. Orientations and characteristics of one or more objects in the vicinity of an object of interest may also be determined.

12 Claims, 6 Drawing Sheets

(52) U.S. Cl.
CPC ............... *G06T 2207/10124* (2013.01); *G06T 2207/20081* (2013.01); *G06T 2207/20084* (2013.01); *G06T 2207/30052* (2013.01)

(58) Field of Classification Search
CPC . G06T 2207/10124; G06T 2207/20081; G06T 2207/20084; G06T 2207/30052; G06T 7/0012; G06T 7/62; G06T 7/74
See application file for complete search history.

(56) References Cited

U.S. PATENT DOCUMENTS

| | | |
|---|---|---|
| 2011/0019884 A1 | 1/2011 | Blau |
| 2015/0238271 A1* | 8/2015 | Wollowick ............... A61B 6/12 600/436 |
| 2016/0100909 A1* | 4/2016 | Wollowick ................ G06T 7/33 600/424 |
| 2016/0157751 A1* | 6/2016 | Mahfouz ................. A61B 5/062 600/409 |
| 2016/0278926 A1 | 9/2016 | Song |
| 2017/0128135 A1* | 5/2017 | McCarthy ............ A61B 5/1121 |
| 2017/0245942 A1* | 8/2017 | Penenberg ............ G06T 19/20 |
| 2018/0206812 A1* | 7/2018 | Trautwein ............. A61B 6/582 |
| 2018/0342315 A1* | 11/2018 | Giphart ................. G16H 30/40 |
| 2019/0029757 A1* | 1/2019 | Roh ....................... G16H 50/00 |
| 2019/0090962 A1* | 3/2019 | Boettner ................ A61B 34/20 |
| 2019/0133693 A1* | 5/2019 | Mahfouz ................ G06T 7/579 |
| 2020/0188026 A1* | 6/2020 | de Souza ............ A61B 5/4851 |
| 2020/0197107 A1* | 6/2020 | Ryan .................... A61B 90/361 |

FOREIGN PATENT DOCUMENTS

| | | | |
|---|---|---|---|
| JP | 201088892 | 4/2010 | |
| WO | WO-2016123700 A1 * | 8/2016 | ........... A61F 2/4609 |

\* cited by examiner

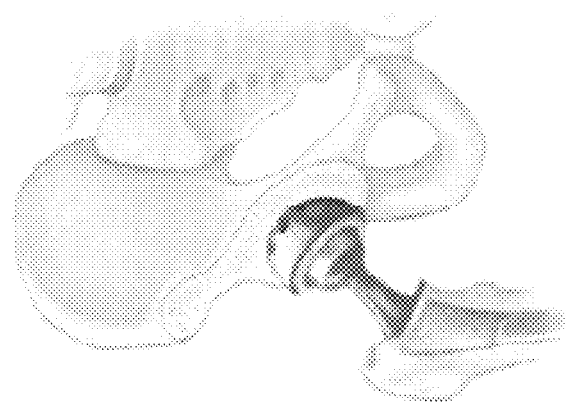
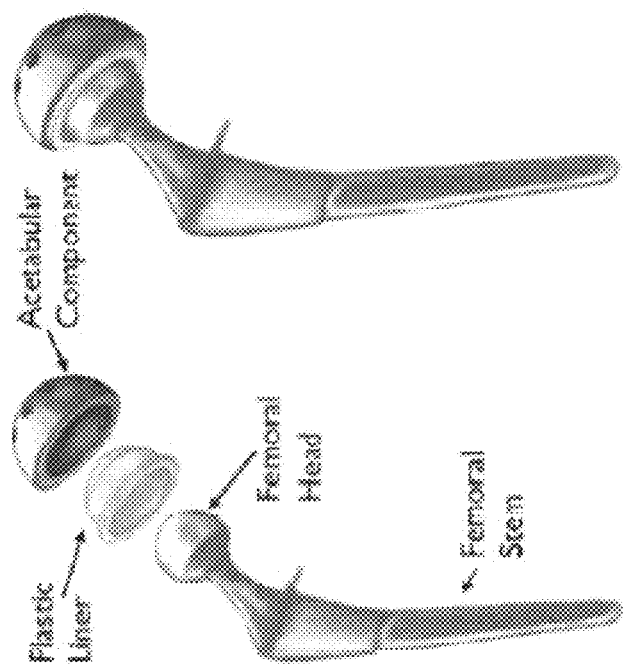
FIG. 4A  FIG. 4B  FIG. 4C  FIG. 4D

| Method | Interobserver reliability | Intraobserver reliability |
|---|---|---|
| | ICC (95% CI) | ICC (95% CI) |
| CT | 0.960 (0.904 to 0.983) | 0.983 (0.959 to 0.993) |
| Lewinnek | 0.933 (0.844 to 0.966) | 0.968 (0.946 to 0.980) |
| Widmer | 0.932 (0.873 to 0.961) | 0.965 (0.945 to 0.978) |
| Orthogonal | 0.936 (0.751 to 0.973) | 0.954 (0.916 to 0.973) |
| Area | 0.992 (0.977 to 0.998) | 0.998 (0.996 to 0.999) |

ICC, intraclass correlation coefficients; CI, confidence interval

FIG. 6

METHODS OF CLASSIFYING AND/OR DETERMINING ORIENTATIONS OF OBJECTS USING TWO-DIMENSIONAL IMAGES

CROSS-REFERENCE TO RELATED APPLICATIONS

This application claims the benefit of U.S. Provisional Application No. 62/715,891, filed Aug. 8, 2018, and U.S. Provisional Application No. 62/818,929, filed Mar. 15, 2019. The contents of these prior applications are incorporated herein by reference.

BACKGROUND OF THE INVENTION

The present invention generally relates to methods for measuring orientations of objects that may be present or placed in a body or other object, as a nonlimiting example, a prosthesis or prosthetic implant in a subject, all of which will hereinafter simply be referred to as "implant(s)" as a matter of convenience. The invention particularly relates to methods of obtaining information regarding an implant that involve analyzing two-dimensional images thereof to determine the orientation of the implant within a subject, optionally various characteristics of the implant, as nonlimiting examples, type, size, material, make, and/or model, and optionally the orientation and characteristics of objects in the vicinity of the implant and visible in the same image to determine a relative orientation of the implant to nearby objects.

FIGS. 4A, 4B, and 4C contain images that schematically represent a total hip replacement implant composed of components including an acetabular component ("cup"), a plastic liner, a femoral head, and a femoral stem. Malposition of the acetabular cup after total hip arthroplasty (THA) is important to assess due to associated risk of impingement, dislocation, and accelerated wear. Metal objects are radiopaque in x-ray images, as readily seen in the x-ray image of the total hip replacement implant in FIG. 4D. As such, radiopaque images of implanted acetabular cups have been utilized to assess their orientation. Implant models have unique designs and thus unique radiographic signatures on an x-ray image. These characteristic features can be used to identify the implant size, type, material, make, and model within a radiopaque image.

Both computed tomography (CT) scans and plain two-dimensional (2D) radiographs (also referred to herein as radiographic images) have been used to measure acetabular cup orientation. FIG. 5 represents the current convention where acetabular cup orientation is described by its inclination and anteversion angles (RI, RA) from, respectively, the sagittal and coronal planes of a human body.

While CT three-dimensional reconstruction is considered to be the most accurate radiographic assessment of acetabular cup orientation, plain radiographs are frequently employed in its place due to the additional radiation exposure and cost to the patient associated with CT scans. Since plain radiographs produce a 2D image, measuring implant orientation that is not orthogonal or parallel to the plane of the image (i.e., anteversion and inclination) can be difficult. While various methods exist for measuring acetabular cup orientation from radiographs, significant variability has been reported on the accuracy of these methods. One contribution to the variability reported may be the dependency these methods have on radiographically obscured points. Several conventional methods rely on accurate visualization and definition of an elliptical opening of the acetabular cup on radiographs. However, this opening is masked by the radiopacity of the acetabular cup and further hidden by the femoral head. Furthermore, the clarity of the opening is variable given its dependency on acetabular cup material, contour, and thickness. These methods have reported a standard deviation up to 10.8°, span upwards of 20° relative to CT measurements, inter-observer reliability as low as 0.747, and intra-observer reliability as low as 0.746.

In cases where a subject requires the replacement of a failed implant, a critical part in pre-operative planning for the orthopaedic surgeon involves the identification of the failed implant, which generally involves identifying its type, size, material, make, and/or model. This step is critical to the surgeon in deciding what materials are necessary for the surgery. Studies have reported cases where surgeons were unable to pre-operatively identify the implant, necessitating that at least twice the number of implants must be brought to the operating room, and resulted in increased time for the surgery, increased healthcare cost, and higher complexity of the surgery.

In view of the above, it can be appreciated that it would be desirable if alternative methods were available for measuring orientations of one or more components of an implant and/or identifying implants, and which may be capable of at least partly overcoming or avoiding problems, shortcomings or disadvantages noted above as being associated with existing methods.

BRIEF DESCRIPTION OF THE INVENTION

The present invention provides methods suitable for accurately and precisely measuring orientations of objects, as nonlimiting examples, implants, and optionally one or more objects in the vicinity of an implant, utilizing two-dimensional radiographs, and optionally also identifying such objects through characteristics thereof that are identifiable in a two-dimensional radiograph.

According to one aspect of the invention, a method is provided for determining a three-dimensional orientation of an object, and optionally other characteristics of the object, based on its area projected onto a two-dimensional image and known or measured geometry.

According to another aspect of the invention, a method is provided for determining a three-dimensional orientation of a first object that is partially obscured by a second object based on a two-dimensional image of the first and second objects. The method involves measuring a combined two-dimensional area of the first and second objects as displayed in the two-dimensional image. The combined two-dimensional area is then used to determine the three-dimensional orientation of the first object by accounting for a measured or estimated two-dimensional area of overlap between the first and second objects, a measured or estimated two-dimensional area of the first object, and a measured or estimated two-dimensional area of the second object. This area of overlap may be estimated with known areas and measurements of the first and second objects and measured, known, or assumed orientations of the first and second objects. Two-dimensional areas may be estimated for first and second objects having known or measured geometries and shapes.

A particular but nonlimiting application of the method described above is to employ the method to determine the three-dimensional orientation of an acetabular cup of a hip implant based on its two-dimensional area displayed in a two-dimensional radiographic image, wherein the acetabular cup is partially obscured by the femoral head of the hip implant in the two-dimensional radiographic image.

Other aspects include methods capable of accurately and precisely identifying characteristics of one or more objects that are identifiable in a two-dimensional radiographic image, as nonlimiting examples, the type, size, material, make, and/or model of an implant, and optionally the orientation and characteristics of one or more objects in the vicinity of the implant and visible in the same two-dimensional radiographic image to determine a relative orientation of the implant to nearby objects. Such a method comprises image processing techniques that identify an implant in question or components thereof (as nonlimiting examples, a total hip arthroplasty, femoral stem, acetabular cup), then identify features of the implant, and subsequently use the features to predict characteristics of the implant, for example, the type, size, material, make, and/or model of the implant. The method may be further applied to structures in the vicinity of the implant, for example, characterizing structures and tissues in the vicinity of the implant and visible in the same two-dimensional radiographic image. Such tissues and structures include, but are not limited to, the pelvis and femur, whose identities and orientations can be utilized to determine the orientation of the implant relative to these structures.

According to another aspect of the invention, a method is provided for determining the three-dimensional orientation of an acetabular cup of a hip prosthesis that is partially obscured by a femoral head of the hip prosthesis based on a two-dimensional radiographic image of the acetabular cup and the femoral head cup after the hip prosthesis has been implanted in a subject. The method includes measuring a first dimension equal to a diameter of the acetabular cup, measuring a second dimension equal to a maximum distance between a posterolateral edge of an opening of the acetabular cup and a point on an exterior surface of the acetabular cup along an axis thereof, and determining the orientation of the acetabular cup based on the measured first and second dimensions.

Still other aspects include methods that apply any of the aforementioned methods to a convolutional neural network, which as used herein refers to a type of artificial intelligence where a program is able to learn a relationship between many inputs and their corresponding outputs. In the context of the aforementioned methods, a convolutional neural network can be employed as a means of automating an otherwise manual process of accurately and precisely identifying characteristics of objects that are identifiable in a two-dimensional radiographic image.

Depending on the particular application or purpose of the method employed, technical effects of the methods described above can include the ability to measure the orientation of an implant (and/or components thereof) in two-dimensional radiographic images in a manner that is significantly more accurate and precise than conventional methods that utilize two-dimensional radiographic images, and/or the ability to identify characteristics of an implant, such as its type, size, material, make, and/or model.

Other aspects and advantages of this invention will be appreciated from the following detailed description.

BRIEF DESCRIPTION OF THE DRAWINGS

FIG. 1A shows dimensions (TL, D2) for calculations used in an "orthogonal method" of the invention, and FIG. 1B shows a combined two-dimensional area for calculations used in an "area method" of the invention.

FIGS. 4A, 4B, 4C, and 4D are images depicting a conventional prosthesis used for a total hip replacement. FIGS. 4A and 4B are, respectively, exploded and assembly views schematically representing the various components of the implant, FIG. 4C schematically represents the implant as implanted within a human subject, and FIG. 4D shows a radiograph of a subject's hip having the implant implanted therein after total hip arthroplasty (THA).

FIG. 6 contains a table that presents data obtained during investigations leading to the present invention and includes inter-observer and intra-observer reliability for CT three-dimensional reconstruction measurements (CT) and the Widmer, Lewinnek, orthogonal, and area methods.

DETAILED DESCRIPTION OF THE INVENTION

Disclosed herein are methods suitable for ascertaining the three-dimensional (3D) orientation of an object, a particular but nonlimiting example of which is an implant surgically placed in a subject, using measurements obtained from a two-dimensional image. Although it is foreseeable and within the scope of the invention that methods disclosed herein could be used to measure the orientation of various implants (for example, femoral, knee, or shoulder replacements) or other objects captured in various types of two-dimensional images (for example, radiographic images or photographs), for convenience the methods will be discussed hereinafter in reference to the orientation of an acetabular cup component of a hip prosthesis after total hip arthroplasty (THA) based on a two-dimensional radiographic image (for example, a fluoroscopic or plain radiographic image).

Methods disclosed herein can be extended to identify characteristics of an object, as nonlimiting examples, the type, size, material, make, and/or model of an implanted prosthesis. Such methods can also be extended to determine the orientations and characteristics of objects that are visible in the same image as an object of interest, for example, bones and other objects in the vicinity of an implanted prosthesis, to determine the relative orientation of the object of interest to other objects in its vicinity.

Two embodiments described in detail herein will be referred to as the "orthogonal method" and the "area method." Both of these methods are configured to minimize measurement assumptions by the user to allow for a more accurate and precise result relative to conventional methods. It is believed that these methods provide a more focal standard deviation relative to conventional methods of analyzing two-dimensional radiographs while allowing for less radiation exposure relative to a CT (computed tomography) scan performed during standard CT three-dimensional reconstruction.

Figure 1B:
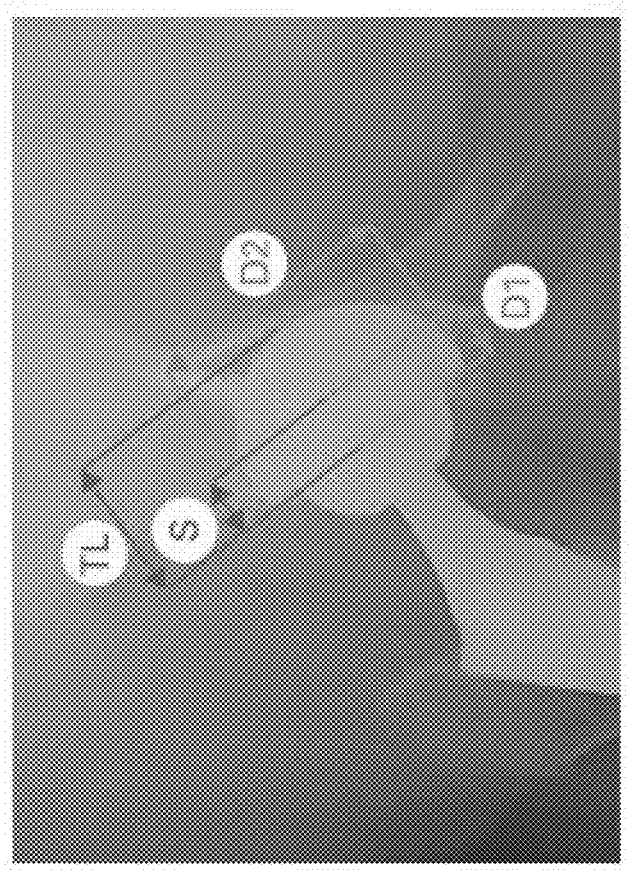
FIGS. 1A and 1B are two plain radiographs representing aspects of measurement methods in accordance with certain nonlimiting embodiments of the invention.
Figure 1A:
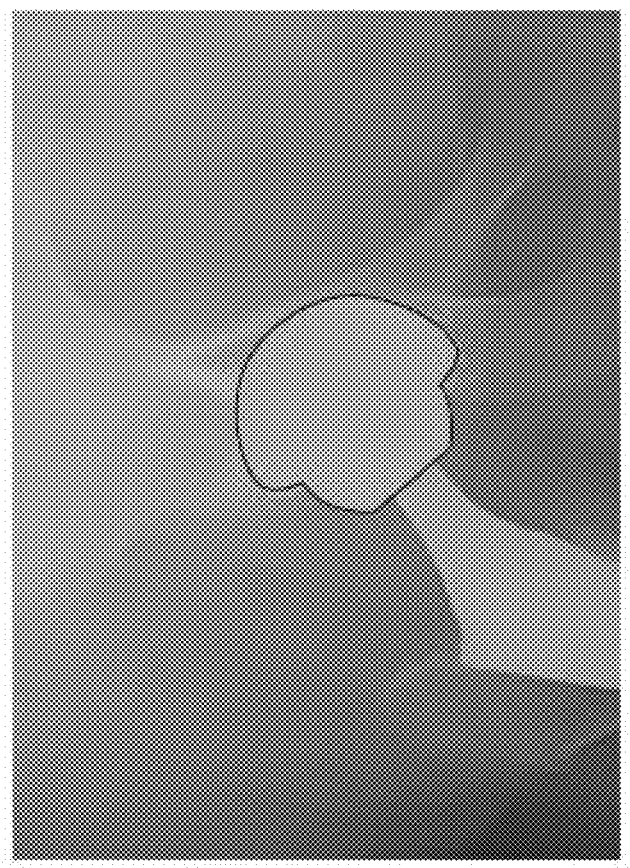

The orthogonal method uses the following equation to identify the acetabular cup orientation angle.

$$\theta = \arcsin\left(\frac{2D_3}{D_2} - 1\right)$$

with $D_2$ and $D_3$ being dimensions represented in FIG. 1A as D2 and TL, respectively. Like many other anteversion equations, this equation is similarly subject to the identification of the edge of the anterolateral ellipse border that is frequently overshadowed by the femoral head of the implant. However, the orthogonal method only requires the identification of one of the two edges of the ellipse. An advantage of this method is that the above-noted equation utilizes readily identifiable in a plain two-dimensional radiographic image, namely, the diameter of the acetabular cup (D2 in FIG. 1A) and the superior edge of the acetabular cup (to determine TL in FIG. 1A). It is unnecessary to identify the anteromedial cup margin, thereby limiting measurement of poorly defined margins to the posterolateral cup border.

The area method determines the three-dimensional orientation of the acetabular cup based on a measurement of its radiopaque area captured in a two-dimensional radiographic image, specifically the acetabular cup and the femoral head or acetabular cup alone. As such, this method determines orientation of an implant not only based on the measurement of its two-dimensional area as displayed on a two-dimensional image, but also based on the measurement of an object that partially obscures it. Since the method relies on area measurements in a two-dimensional image, it requires the radiographic image to be calibrated to the measurements to be taken. For the purposes of investigations described below, measurements were calibrated with the known diameter of a femoral head, though this may also be performed with a calibration ball, a cup diameter, or any other known dimension of an object that is visible in the two-dimensional image.

FIG. 1B represents a radiograph wherein a border defined by the combination of the acetabular cup and femoral head is outlined, and the combined two-dimensional area of the acetabular cup and femoral head enclosed therein is highlighted. This highlighted area is equal to a two-dimensional area of the acetabular cup and a two-dimensional area of the femoral head less the two-dimensional area of overlap between these two components. The areas of the two individual components may be determined based on known measurements of the implant or may be measured directly on the radiopaque prosthesis of the radiograph. By measuring the highlighted area and subtracting it from the combined two-dimensional area of the two components, one can determine the two-dimensional area of overlap between these two components. This value relates to the anteversion angle (RA, measured from the coronal plane of the human body) as follows:

$$\text{Area of overlap} = \pi DF^2 \frac{\sin^{-1}\left(\frac{2\left(\frac{AoD}{2}(\sin(\theta)+1)-T\right)}{FD}-1\right)+90}{2*360} +$$

$$\frac{1}{2}\left(\left\|\left(\frac{AoD}{2}(\sin(\theta)+1)-T\right)-\frac{1}{2}FD\right\|-\frac{1}{2}FD\right)^2$$

$$\tan\left(\sin^{-1}\left(\frac{2\left(\frac{AoD}{2}(\sin(\theta)+1)-T\right)}{FD}-1\right)\right)+AoD^2\sin(\theta)$$

$$\left(\frac{\pi}{180}\tan^{-1}\left(\frac{2\left(\left(\frac{AoD}{2}(\sin(\theta)+1)-T\right)+T-\frac{AoD}{2}\right)}{2*\left\|\left\|\left(\frac{AoD}{2}(\sin(\theta)+1)-T\right)-\frac{1}{2}FD\right\|-\frac{1}{2}FD\right\|}\right)+1\right)-$$

$$\frac{\left\|\left\|\left(\frac{AoD}{2}(\sin(\theta)+1)-T\right)-\frac{1}{2}FD\right\|-\frac{1}{2}FD\right\|}{2}$$

$$\left(\left(\frac{AoD}{2}(\sin(\theta)+1)-T\right)+T-\frac{AoD}{2}\right)$$

where $\theta$ represents the planar anteversion, T and AoD are the thickness and outer diameter, respectively, of the acetabular cup, and FD is the diameter of the femoral head.

According to a preferred aspect of the invention, the area method is implemented by a system configured to analyze a radiograph, having the border of the combined components outlined by a user, to determine the combined two-dimensional area within the border and simultaneously measure other values that may be necessary for determining the anteversion angle, such as the femoral head diameter, femoral head truncation (i.e., where the femoral head sphere is cut), acetabular cup outer diameter, and the acetabular cup inner diameter. It is foreseeable and within the scope of the invention that the system may be configured to identify the border of the combined components itself.

Nonlimiting embodiments of the invention will now be described in reference to experimental investigations leading up to the invention. These investigations were intended to evaluate the accuracy and precision of the orthogonal and area methods against other known plain radiographic methods, and against a CT three-dimensional reconstruction measurement. The conventional methods used in these investigations are described in the publications Lewinnek et al., *Dislocations after total hip-replacement arthroplasties*, The Journal of Bone and Joint Surgery, American volume, 1978; 60(2):217-220 (referred to herein as the "Lewinnek method") and Widmer K., *A simplified method to determine acetabular cup anteversion from plain radiographs*, The Journal of arthroplasty, 2004; 19(3):387-390 (referred to herein as the "Widmer method").

In particular, the orthogonal, area, Widmer, and Lewinnek methods were each used to determine the acetabular cup anteversion angle on 160 anteroposterior (AP) pelvis radiographs for 160 total hip replacements (130 patients) performed between January 2012 and December 2015. In addition, twenty-one CT scans were included, allowing for assessment via three-dimensional reconstruction. For the CT three-dimensional reconstructions, anteversion angles were measured relative to the functional coronal plane. Each of the two-dimensional methods were compared to the CT measurements, with a positive value representing an overestimation on planar radiography compared to CT-based measurement. The methods were performed on each radiograph by multiple users.

Whisker and box plots were used to represent the difference between each method and the CT-based measurement. Using Pearson's regression and coefficient of determination, the linearity of each measurement was determined with increasing anteversion according to CT-based measurement. The inter- and intra-observer reliability was represented with intraclass correlation coefficients (ICC) and a 95% confidence interval (CI). The two-way random-effects intraclass correlation model and absolute agreement was used for this calculation. An ICC of one represented perfect reliability, while zero represented no relationship. The resulting inter-observer reliability for each method is disclosed in a table shown in FIG. 6. There were no acetabular cups with retroversion according to CT and cross-table radiograph assessment.

Figure 2:
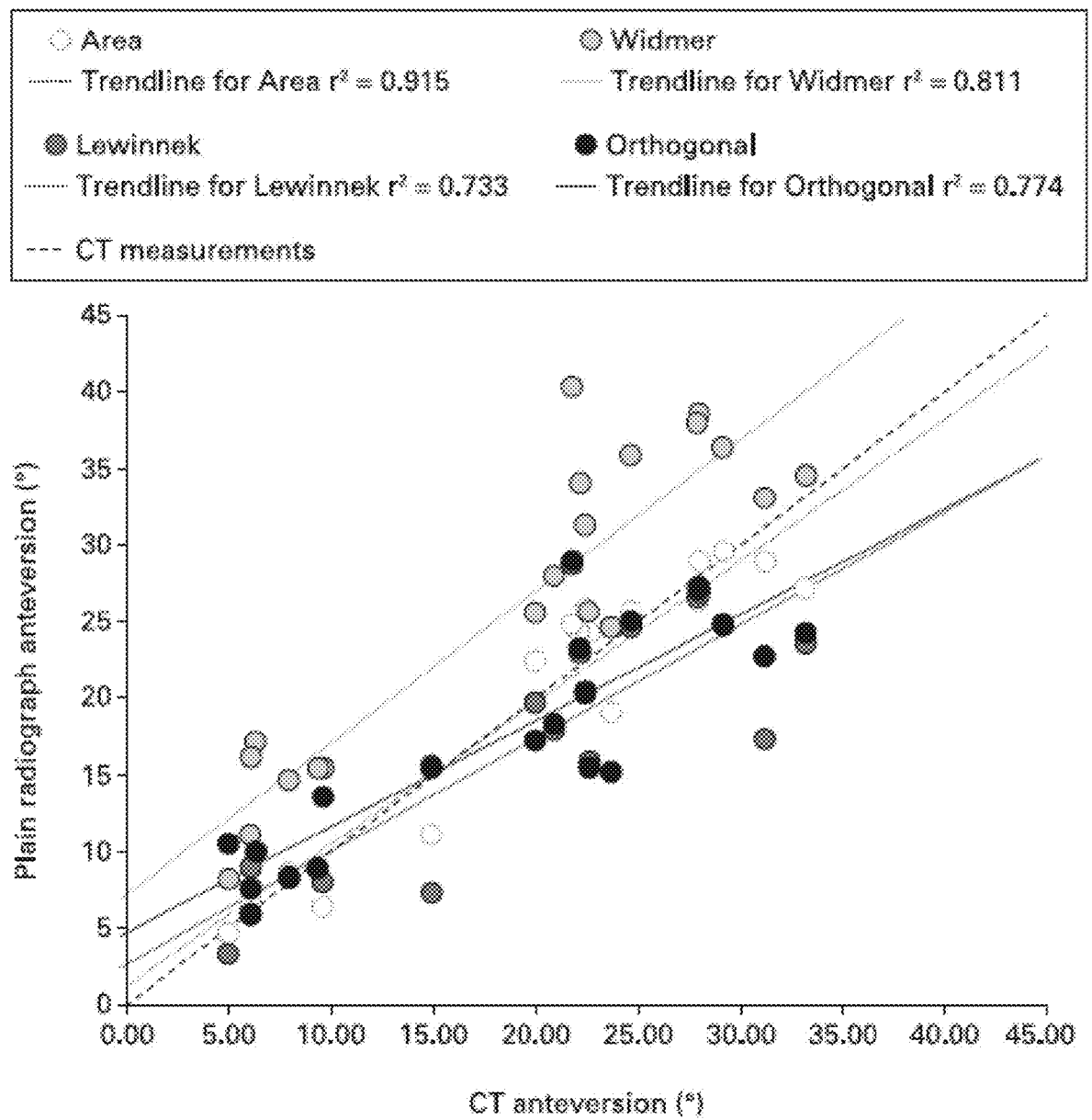
FIG. 2 is a graph representing measured anteversion obtained by the above-noted area ("Area") and orthogonal ("Orthogonal") methods as well as obtained by "Widmer" and "Lewinnek" methods (discussed below), all of which are plotted against CT three-dimensional reconstruction measurements ("CT measurements"). Measurements were averaged between multiple users. Pearson correlation coefficient (r) and coefficient of determination ($r^2$) were calculated for each method against CT three-dimensional reconstruction measurements.
Figure 3:
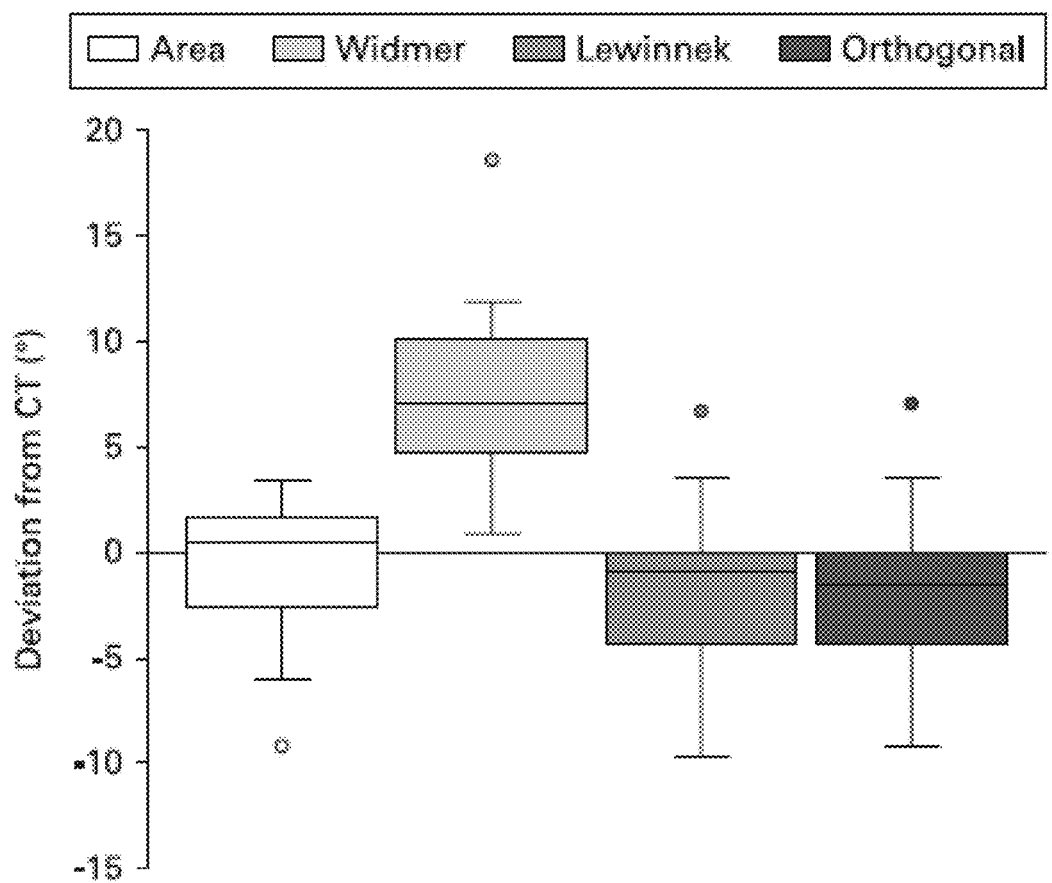
FIG. 3 is a graph representing Whisker and box plots for the area, orthogonal, Widmer, and Lewinnek methods as compared to CT three-dimensional reconstruction measurements ("CT"). The horizontal line in each box represents the median value, the outer regions of each box represent the interquartile range, the outside lines associated with each box represent the exclusive range, and the outside points represent outliers.
Figure 5:
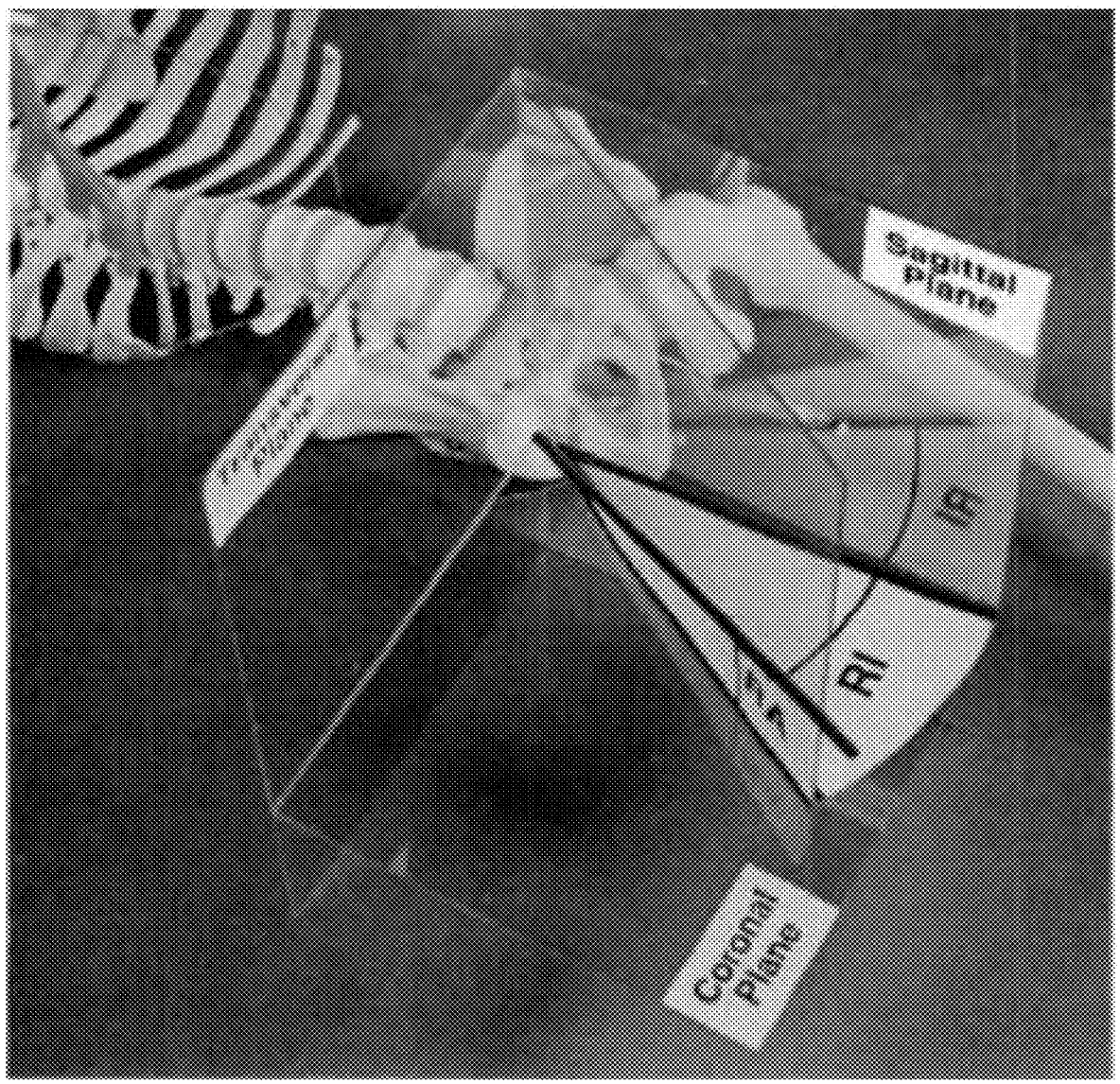
FIG. 5 represents the current convention by which the three-dimensional orientation of an acetabular cup can be described by its inclination and anteversion angles (RI, RA) from, respectively, the sagittal and coronal planes of the human body.

The mean differences from CT-based measurements were −0.2° (standard deviation (SD), 2.7°), −1.2° (SD, 4.5°), −2.3° (SD, 4.8°), and 6.9° (SD, 4.5°) for the area, orthogonal, Lewinnek, and Widmer methods, respectively (FIG. 3). The Lewinnek, orthogonal, and area methods resulted in statistically lower recorded anteversion than the Widmer method with (p<0.0001). The Lewinnek method resulted in a statistically lower anteversion measurement than the orthogonal (−1.6°; p<0.001) and area methods (−1.2°; p=0.004). The orthogonal method was not statistically different from the area method (−0.9°; p=0.293). The coefficients of determination ($r^2$) of the methods with respect to CT-based measurement were 0.915, 0.811, 0.774, and 0.733 for the area, Widmer, orthogonal, and Lewinnek methods, respectively (FIG. 2). The variability of measurements between observers averaged 0.37°, 3.110, 3.17°, and 3.80° for the area, Lewinnek, orthogonal, and Widmer methods. The area method provided the greatest accuracy and precision, within 10 of CT three-dimensional reconstruction within the range of 10 to 30° of measured radiographic anteversion.

In the above described investigations, the area method was determined to be the most reliable radiographic measurement method tested (intra- and inter-observer reliability at 0.998 and 0.992, respectively). Furthermore, this method most closely mirrored the anteversion measured from the CT three-dimensional reconstruction (coefficients of determination ($r^2$) of 0.915).

It is believed that the standard deviation of 2.7° observed for the area method was largely contributed by pelvis positioning in the radiographs. It has been reported that pelvis orientation and posture significantly affect measured anteversion, with 1° of pelvic tilt changing anteversion by about 0.7 to 0.8°. Given the intended application of these methods to a diverse clinical setting, no radiographs were excluded from the investigations despite variability in posture and quality. When controlling for pelvic orientation by having users separately assess the same radiograph, variability averaged 0.37° and inter-observer reliability at 0.992. Thus, these investigations indicated that the area method is precise, but measured anteversion is similarly dependent on pelvic orientation. This conclusion was supported by an adjunct study involving radiographic measurement of 160 acetabular cup orientations when compared to anteversion measured by an iPhone accelerometer. In this experiment, the coefficient of determination improved from 0.915 to 0.997; equivalent to a Pearson correlation coefficient of 0.999.

In further investigations, the application of artificial neural networks was evaluated to determine their ability to both automate the described measurement technique performed on an implant and identify the implant, thus offering a timely and accurate computational solution to a common problem. One of the most advanced forms of artificial intelligence to date is known as "deep learning" and includes artificial neural networks. When plotted out, an artificial neural network's architecture appears much like neurons and dendrites, intended to mirror human thought. In the context of the ability to identify an implant, the use of a convolutional neural network would also be able to provide a percent confidence that an implant as been accurately classified, offering additional valuable information to the user.

For purposes of investigating artificial neural networks, the above methods using two-dimensional images were applied to 2909 unique AP radiographs of the pelvis, each with a corresponding prosthesis orientation determined from each radiograph using the area method described above. A convolutional neural network was then trained with a given input of each radiograph and a corresponding output of the implant orientation from the area method (obtained by hand). The purpose of this was to create a convolutional neural network (an automated method) that may take any similar radiograph to that trained as an input and the output would be the orientation of the implant. The convolutional neural network, after an initial training, was able to achieve an accuracy of within 4.23°+4.26° from hand measurements. The use of a convolutional network also allowed a speedy calculation, taking only 0.0211 seconds to achieve results from one image. The accuracy of the convolutional neural network may be further optimized with Bayesian optimization, where the parameters used to train the convolutional neural network may be optimized under this method. This should enable greater accuracy and precision than that obtained by the procedure described above. Similarly, the structure of the convolutional neural network may be further adjusted for optimization.

The above methods were further applied to 2909 unique AP radiographs of the pelvis and corresponding convolutional neural network to classify each pixel in the image as the pelvis, femur, prosthesis femoral stem component, and prosthesis acetabular component. This information was applied to the 2909 images and used to train the convolutional neural network. The preliminary results offered pixel classification accuracy of 98%, meaning every pixel in the image provided would be classified with 98% accuracy of either a pelvis, femur, prosthetic femoral stem, or prosthetic acetabulum. This may also be further optimized with Bayesian optimization and the structure of the convolutional neural network.

The above methods are believed to be applicable to a similar number of CT or MRI scans of the pelvis. Doing so would allow one of ordinary skill in the art to identify the true orientation of a component of interest relative to any other structure appearing in a two-dimensional image. In the example above, the orientation of the acetabular cup was determined relative to a patient's anterior pelvic plane, although methods disclosed herein are not limited thereto. Cup orientation obtained with several thousand images can be used to train a convolutional neural network, thus providing a means for automating a program to determine the three-dimensional orientation of the acetabular cup relative to nearby structures using a two-dimensional radiograph as its input.

In view of the above, aspects of the present disclosure include applying measurements of an implant orientation to train a convolutional neural network. The use of a convolutional neural network enables a computer to automate the described methods, thereby measuring the orientation of an implant (or other object) from a two-dimensional image based on the training data provided. Briefly, it does so by optimizing a relationship between its inputs and corresponding outputs. Such a method may be applied to numerous images as a means to train the convolutional neural network.

Additional aspects of the present disclosure involve identifying structures and tissues in the vicinity of an implant and visible with the implant in a two-dimensional image as a means to ascertain an orientation of the implant relative to nearby structures/tissues. For example, a convolutional neural network as described above may be employed to identify the nearby structures in the two-dimensional images discussed above. In a particular example, data obtained from three-dimensional (3D) images, as an example, a computed tomography (CT) or magnetic resonance imaging (MRI) scan, were used to accurately identify true orientation of an object of interest relative to nearby structures of interest. The convolutional neural network was then trained on the original two-dimensional image with the true orientation obtained from the three-dimensional image. In essence, doing so enabled the convolutional neural network to identify structures in the two-dimensional image that may determine the relative three-dimensional orientation.

A nonlimiting example of an application for the above is to identify the orientation of the acetabular component relative to the functional coronal plane of the pelvis. The functional coronal plane is a plane defined by the right and left anterior superior iliac spine (ASIS) and the pubic symphysis. Once this orientation is determined by numerous patients accurately from three-dimensional imaging (e.g., CT or MRI), the patient's corresponding 2D radiographs can be obtained. The 2D radiographs may be used as the input to the convolutional neural network, while the 3D orientation will be the output, thereby presenting a method to teach a program to automatically determine the 3D orientation of an object of interest relative to nearby structures of interest from a 2D image.

Convolutional neural networks are believed, at this time, to be a suitable version of artificial intelligence and deep learning for use in the methods described above due to their application to a matrix. In this case, the matrix is the image (a matrix of red, green, and blue values). These techniques may also be applied to other available version of artificial intelligence similarly readily applicable to images.

Given the ready application to images of convolutional neural networks, a convolutional neural network can be taught to identify characteristics of an object of interest in an input 2D image, as nonlimiting examples, the make, model, type, material, and size of an implant in the input 2D image. As an example, the operative notes of 1594 total hip arthroplasty procedures were identified that contained mention of one of eight commercially available femoral stems. From these, a convolutional neural network was developed from 1410 AP Hip radiographs, after which the neural network was tested on a subsequent 706 AP Hip radiographs. The neural network was then run on an iPhone 6 to evaluate its potential use in app design. The neural network achieved 100.00% accuracy on the 1410 learning radiographs, and achieved 95.15% accuracy in classifying femoral stem constructs when tested on the novel 706 radiographs. The neural network also displayed the probability (confidence) of the femoral stem classification for any input radiograph, and on the basis of general model alone was able to achieve percent confidence ranging from 91.31% to 99.97% for seven different models. The neural network averaged a runtime of 1.03+0.05 seconds for an iPhone 6 to calculate from a given radiograph. From this, it was concluded that a relatively simple convolutional neural network is capable of generating high accuracy in identifying implant designs, and can run on a personal device to offer additional benefits to a learning resident or attending surgeon.

Another application is to use radiographs as inputs, dual-energy X-ray absorptiometry (DXA, or DEXA) scan results as outputs, and thus present an option to create a convolutional neural network that may use radiographs to predict DEXA scan results as a means to predict osteopenia or osteoporosis.

While the invention has been described in terms of particular embodiments and investigations, it should be apparent that alternatives could be adopted by one skilled in the art. For example, the methods may be used to determine the orientation of implants or other objects other than acetabular cups of a hip prosthesis, the implant measured and its components could differ in appearance and construction from the embodiments described herein and shown in the drawings, and the measurements may be used to analyze image types other than radiographs. Accordingly, it should be understood that the invention is not necessarily limited to any embodiment described herein or illustrated in the drawings. It should also be understood that the phraseology and terminology employed above are for the purpose of describing the illustrated embodiments and investigations, and do not necessarily serve as limitations to the scope of the invention. Therefore, the scope of the invention is to be limited only by the following claims.

The invention claimed is:

1. A method of determining a three-dimensional orientation of a first object that is partially obscured by a second object, the first and second objects having known or measured geometries and shapes, the method comprising:
    capturing radiopaque areas of each of the first and second objects in a single two-dimensional radiographic image, the radiopaque areas comprising a first two-dimensional area of the first object, a second two-dimensional area of the second object, and a two-dimensional area of overlap of the first and the second two-dimensional areas of the first and second objects within the two-dimensional radiographic image;
    calibrating the two-dimensional radiographic image to a known dimension of at least one of the first object, the second object, or another object that is visible in the two-dimensional radiographic image;
    determining the first and second two-dimensional areas of the first and second objects within the two-dimensional radiographic image;
    identifying an outline of the radiopaque areas of the first and second objects displayed in the two-dimensional radiographic image;
    measuring a combined two-dimensional area of the first and second objects within the outline; and
    subtracting the combined two-dimensional area from the first and the second two-dimensional areas of the first and second objects to determine the two-dimensional area of overlap and therefrom the three-dimensional orientation of the first object.

2. The method of claim 1, further comprising determining other characteristics of the object, wherein the other characteristics of the object comprise one or more of make, model, and material of the object based on the area thereof projected onto the two-dimensional radiographic image and the known or measured geometry and radiographic opacity thereof.

3. The method of claim 1, further comprising determining a three-dimensional orientation of the first object relative to the second object in the two-dimensional radiographic image.

4. The method of claim 1, wherein the method uses artificial intelligence to determine the three-dimensional orientation of the first object.

5. The method of claim 1, wherein the method uses deep learning to determine the three-dimensional orientation of the first object.

6. The method of claim 1, wherein the method uses a convolutional neural network to determine the three-dimensional orientation of the first object.

7. The method of claim 1, wherein the first object is a first prosthetic component.

8. The method of claim 7, wherein the second object is a second prosthetic component.

9. The method of claim 8, wherein the first and second prosthetic components are an acetabular cup and a femoral head of a hip prosthesis.

10. The method of claim 8, further comprising determining other characteristics of the first object based on its area projected onto the two-dimensional radiographic image and the known or measured geometry thereof.

11. The method of claim 10, wherein the other characteristics of the first object comprise one or more of make, model, and material of the first object based on the area thereof projected onto the two-dimensional radiographic image and the known or measured geometry and radiographic opacity thereof.

12. The method of claim 10, further comprising determining the orientation and characteristics of the second object and determining therefrom a relative orientation of the first object to the second object.

* * * * *